(12) United States Patent
Mishima et al.

(10) Patent No.: US 9,056,029 B2
(45) Date of Patent: Jun. 16, 2015

(54) DISPOSABLE PULL-ON WEARING ARTICLE

(75) Inventors: Yoshitaka Mishima, Kagawa (JP); Kunihiko Katsuragawa, Kagawa (JP)

(73) Assignee: Unicharm Corporation, Ehime (JP)

( * ) Notice: Subject to any disclaimer, the term of this patent is extended or adjusted under 35 U.S.C. 154(b) by 124 days.

(21) Appl. No.: 13/819,731

(22) PCT Filed: Aug. 17, 2011

(86) PCT No.: PCT/JP2011/068586
§ 371 (c)(1),
(2), (4) Date: Feb. 28, 2013

(87) PCT Pub. No.: WO2012/043083
PCT Pub. Date: Apr. 5, 2012

(65) Prior Publication Data
US 2013/0184669 A1      Jul. 18, 2013

(30) Foreign Application Priority Data
Sep. 30, 2010  (JP) ................. 2010-223076

(51) Int. Cl.
*A61F 13/15*  (2006.01)
*A61F 13/49*  (2006.01)
(Continued)

(52) U.S. Cl.
CPC ..... *A61F 13/49012* (2013.01); *A61F 13/49007* (2013.01); *A61F 13/49009* (2013.01);
(Continued)

(58) Field of Classification Search
CPC ..... A61F 13/496; A61F 13/539; A61F 13/49; A61F 13/49007; A61F 13/49009; A61F 13/49011; A61F 13/49014; A61F 13/49017; A61F 13/49019; A61F 13/49033; A61F 13/49031; A61F 13/4906; A61F 13/49061; A61F 2013/49063

USPC ............ 604/385.24, 385.25, 385.26, 385.27, 604/385.28, 385.29, 385.3
See application file for complete search history.

(56) References Cited

U.S. PATENT DOCUMENTS 6,491,676 B1    12/2002  Suzuki et al.
2006/0282058 A1 12/2006  Otsubo et al.
(Continued)

FOREIGN PATENT DOCUMENTS

| JP | 08-056987 | 3/1996 |
| JP | 11-511664 | 10/1999 |
| JP | 2005-110990 | 4/2005 |
| JP | 2006-141494 | 6/2006 |
| JP | 2006-181172 | 7/2006 |

(Continued)

OTHER PUBLICATIONS

International Search Report from corresponding PCT application No. PCT/JP2011/068843 dated Oct. 11, 2011 (4 pgs).

*Primary Examiner* — Jacqueline Stephens
(74) *Attorney, Agent, or Firm* — Brinks Gilson & Lione

(57) ABSTRACT

A disposable pull-on wearing article including a pant-shaped chassis and an absorbent panel. A pull-on wearing article includes a pants-shaped chassis and an absorbent panel. The chassis has a front portion including a front waist region and part of a crotch region and a rear portion including a rear waist region and part of the crotch region. The front portion has a plurality of front waist elastics extending in a width direction and the rear portion has a plurality of rear waist elastics extending in the width direction. A bottom elastic of the front waist elastics and a bottom elastic of the rear waist elastics are in a stretched state in front peripheral edge portion and rear peripheral edge portion of respective leg-openings and in a relaxed state in a portion of the crotch region defined between a pair of the leg-openings.

20 Claims, 7 Drawing Sheets

(51) Int. Cl.
*A61F 13/494* (2006.01)
*A61F 13/496* (2006.01)
*A61F 13/505* (2006.01)

(52) U.S. Cl.
CPC ..... *A61F13/49014* (2013.01); *A61F 13/49011* (2013.01); *A61F 13/49017* (2013.01); *A61F 13/49019* (2013.01); *A61F 13/49015* (2013.01); *A61F 13/49061* (2013.01); *A61F 13/49413* (2013.01); *A61F 13/49466* (2013.01); *A61F 13/496* (2013.01); *A61F 13/505* (2013.01); *A61F 2013/49063* (2013.01); *A61F 2013/4948* (2013.01)

(56) References Cited

U.S. PATENT DOCUMENTS

2007/0239128 A1* 10/2007 Takada et al. ............ 604/385.25
2009/0312739 A1  12/2009 Umebayahi et al.

FOREIGN PATENT DOCUMENTS

| JP | 2006-346005 | 12/2006 |
| JP | 2008-136515111 | 6/2008 |
| WO | WO 96/23477 | 8/1996 |
| WO | WO 2006/118214 A1 | 11/2006 |

* cited by examiner

DISPOSABLE PULL-ON WEARING ARTICLE

RELATED APPLICATION

This application is a 35 U.S.C. §371 national phase filing of International Patent Application No. PCT/JP2011/068586, filed Aug. 17, 2011, through which and to which priority is claimed under 35 U.S.C. §119 to Japanese Patent Application No. 2010-223076, filed Sep. 30, 2010.

TECHNICAL FIELD

The present invention relates to disposable pull-on wearing articles adapted to be used, for example, in the form of disposable diapers or disposable incontinent pants.

BACKGROUND

Conventionally, disposable pull-on wearing articles are known which include a pant-type chassis and an absorbent panel.

For example, a pull-on diaper disclosed in JP 2006-141494 A (PTL 1) includes a cover sheet and an hourglass-shaped liquid-absorbent body. The cover sheet is doubled up in a crotch region so as to form a pant-shaped chassis which resembles trunks wherein the liquid-absorbent body is joined to an inner surface of the cover sheet. Elastics are attached to the cover sheet's concavely cut out portions to define leg-openings of the pull-on diaper along respective peripheries of these portions. The cover sheet includes, in addition, elastics attached to a front waist region and a rear waist region, respectively.

CITATION LIST

Patent Literature

{PTL 1}: JP 2006-141494 A

SUMMARY

Technical Problem

The pull-on diaper disclosed in PTL 1 is intended to keep the liquid-absorbent body being integral with the cover sheet in close contact with the wearer's body under the effect of the elastics attached to the cover sheet. While the cover sheet and the liquid-absorbent body are separately prepared, if it is tried to pull up the liquid-absorbent body along the wearer's body after the pull-on diaper has been put on the wearer's body, the cover sheet also is pulled up and, as a result, the elastics attached to the cover sheet's concavely cut out portions are likely to remain in close contact with the wearer's thighs. Consequently, on the assumption that the liquid-absorbent body is formed along lateral edges thereof with leakage-barriers adapted to be spaced away toward the wearer's skin under the effect of the elastics, the leg elastics remaining in close contact with the wearer's thighs are apt to interfere with up standing of the leakage-barriers. In consequence, body exudates tend to leak out of the diaper.

An object of the present invention is to provide a disposable pull-on wearing article improved so that leakage-barriers of a bodily fluid absorbent panel can smoothly space away toward the wearer's body without any interference of elastics attached to peripheries of respective leg-openings.

Solution to Problem

The present invention relates to a disposable pull-on wearing article including a pants-shaped chassis which includes a front waist region, a rear waist region and a crotch region each having an inner side facing a wearer's skin, and an absorbent panel extending across the crotch region into the front waist region and the rear waist region and joined to the inner side of the chassis, wherein the chassis is formed with a waist-opening and a pair of leg-openings.

In such pull-on wearing article, the present invention further includes the following features:

the chassis includes a front portion including the front waist region and part of the crotch region and a rear portion including the rear waist region and a part of the crotch region;

the front portion is provided with a plurality of front waist elastics extending in a width direction of the front waist region and spaced apart from each other in a vertical direction of the front waist region;

at least one front lowest elastic lying at a bottom of the front waist elastics is disposed in a stretched state along front peripheral edge portion of the pair of leg-openings and, in the front portion of the crotch region defined between the pair of leg-openings, the at least one front lowest elastic is disposed in a more relaxed state than along the front peripheral edge portions;

the rear portion is provided with a plurality of rear waist elastics extending in a width direction of the rear waist region and spaced apart from each other in a vertical direction of the rear waist region;

at least one rear lowest elastic lying at a bottom of the rear waist elastics is disposed in a stretched state along rear peripheral edge portion of the pair of leg-openings and, in a rear portion of the crotch region defined between the pair of leg-openings, the at least one rear lowest elastic is disposed in a more relaxed state than along the front peripheral edge portions;

the absorbent panel has a front end portion joined to the inner surface of the front waist region, rear end portion joined to the inner surface of the rear waist region and a midsection extending between the front end portion and the rear end portion and not joined to the inner surface of the crotch region; and the absorbent panel is formed on lateral portions in the width direction thereof with containment flaps adapted to be spaced away from the inner surface of the absorbent panel under contraction of elastics extending between the front end portion and the rear end portion.

According to one embodiment of the present invention, opposite lateral portions in the width direction of the chassis extend in the vertical direction to a lower end portion of the absorbent panel located in the crotch region.

According to another embodiment of the present invention, the opposite lateral portions in the width direction of the chassis are prepared separately of the elements forming the front and rear waist regions and panel elements including neither the front waist elastics nor the rear waist elastics are interposed between the front waist region and the rear waist region.

According to even another embodiment of the present invention, the bottom elastic in the front waist elastics and the bottom elastic in the rear waist elastics extend across the crotch region but not to inner thigh areas of the crotch region.

According to still another embodiment of the present invention, the inner thigh areas of the crotch region include none of elastics extending in a front-back direction in a stretched state.

According to yet another embodiment of the present invention, a portion of the front waist region defined below the front end portion of the absorbent panel is uniformly formed with gathers in the entire width direction and a width of this portion of the front waist region is uniform.

According to further another embodiment of the present invention, a portion of the rear waist region defined below the rear end portion of the absorbent panel is uniformly formed with gathers in the entire width direction and a width of this portion of the rear waist region is uniform.

Advantageous Effects of Invention

In the disposable pull-on wearing article according to the present invention, the opposite end portions of the absorbent panel provided with the containment flaps are respectively joined to the inner surfaces of the front and rear waist regions of the pants-shaped chassis but the midsection of the absorbent panel located in the crotch region is not joined to the crotch region of the chassis. In addition, the bottom elastics located on the front portion and the rear portion of the chassis and extending in the width direction of the chassis extend along the front peripheral edge portion or the rear peripheral edge portion of a pair of the leg-openings. In the pull-on wearing article of such arrangement, when it is tried to pull up the absorbent panel along the wearer's body after the wearing article has been put on the wearer's body, the respective bottom elastics on the front and rear peripheral edge portions serving as the leg elastics do not conform to the movement of the absorbent panel to be pulled up. In this way, the leg elastics should not interfere with up standing of the containment flaps of the absorbent panel.

DESCRIPTION OF EMBODIMENTS

On the basis of a disposable pull-on diaper as an example of a disposable pull-on wearing article, details of the present invention will be described hereunder with reference to the accompanying drawings.

Figure 1:
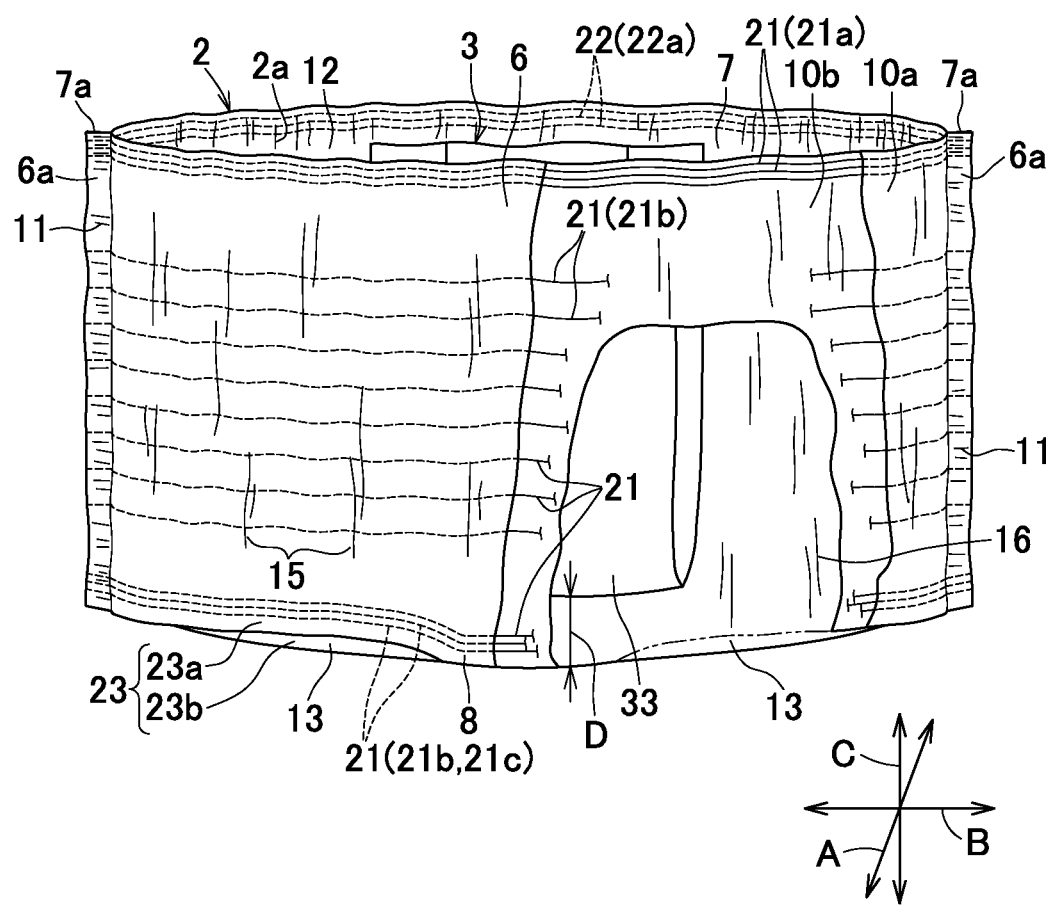
FIG. 1 is a partially cutaway perspective view of a pull-on diaper illustrated as an example of a disposable pull-on wearing article.

FIG. 1 is a partially cutaway perspective view of a disposable pull-on diaper 1, and in FIG. 1, a front-back direction, a width direction and a height direction are indicated by double-headed arrows A, B, C, respectively. In this regard, the height direction C will be sometimes designated hereunder by a vertical direction C. The diaper 1 includes a pant-type chassis 2 and an absorbent panel 3 attached to an inner surface 21 of the chassis 2. The chassis 2 may be designated as trunks-type pants or boxer-type pants and includes a front waist region 6, a rear waist region 7 and a crotch region 8 extending between these front and rear waist regions 6, 7. The chassis 2 is doubled up in the crotch region 8 so that respective lateral edge portions 6a, 7a of the front and rear waist regions 6, 7 may be put flat together and welded together at a pair of series of seams 11. Such chassis 2 is formed with a waist-opening 12 and a pair of leg-openings 13. The front and rear waist regions 6, 7 are formed with many gathers 15 undulating in the width direction B under contraction of front waist elastics 21 and rear waist elastics 22 to be described later. On the inner side of the chassis 2, the absorbent panel 3 doubled up in vicinities of the crotch region 8 extends in the vertical direction C. A midsection 33 of the absorbent panel 3 defining a crotch region of this panel 3 is spaced apart from the crotch region 8 of the chassis 8 by a dimension D.

Figure 2:
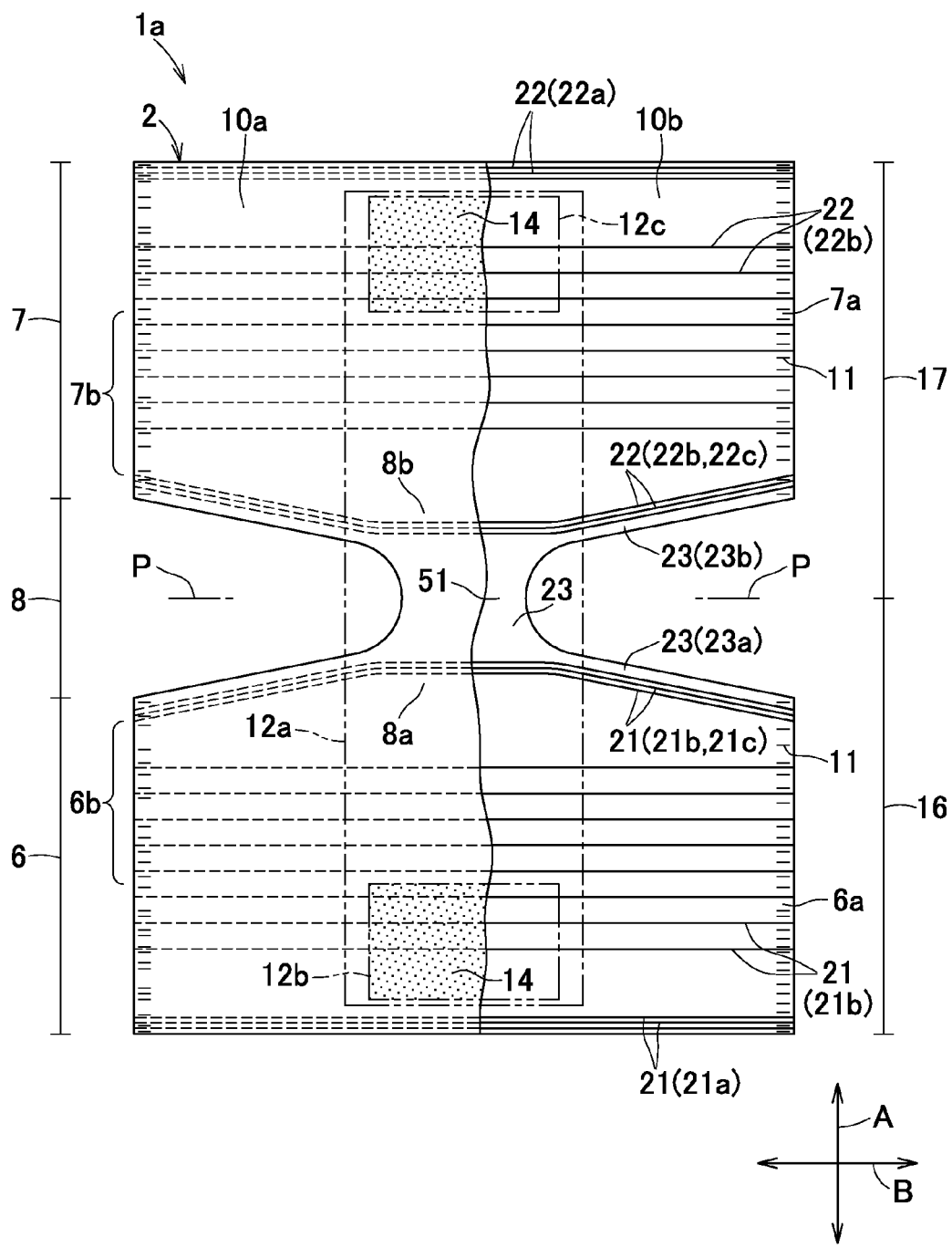
FIG. 2 is a partially cutaway plan view illustrating the diaper in a developed state.

FIG. 2 is a partially cutaway plan view of a developed diaper 1a obtained by unsealing the welded seams arranged along the lateral edge portions 6a, 7a of the diaper 1 illustrated in FIG. 1 and developing the front and rear waist regions 6, 7 and the crotch region 8 in the front-back direction A and in the width direction B. In this regard, only a contour of the absorbent panel 3 is indicated by imaginary line 12a and, in consideration of this, it is possible to designate FIG. 2 to be substantially a partially cutaway plan view of the chassis 2. The chassis 2 in FIG. 2 includes a topsheet 10a and a backsheet 10b overlapping each other and joined to each other with a hot melt adhesive (not shown). Between the topsheet 10a and the backsheet 10b, a plurality of front elastics 21 and a plurality of rear elastics 22 both attached under tension in the width direction B. These elastics 21, 22 are secured under tension, i.e., in a stretched state to the topsheet 10a and/or the backsheet 10b with a hot melt adhesive (not shown). The front elastics 21 lie in a front section 16 of the developed diaper 1a defined by a center line P bisecting a dimension in the front-back direction A of the developed diaper 1a and this front section 16 includes the front waist region 6 and part of the crotch region 8. The rear elastics 22 lie in a rear section 17 defined by the center line P and this rear section 17 includes the rear waist region 7 and part of the crotch region 8.

The front elastics 21 include a plurality of upper elastics 21a extending in parallel to each other along a peripheral edge portion of the waist-opening 12 in FIG. 1 and a plurality of lower elastics 21b lying below the upper elastics 21a as viewed in FIG. 1. Of these lower elastics 21b, at least one lowest elastic 21c extends along front peripheral edge portion 23a of respective peripheral portions 23 of the leg-openings 13 (See FIG. 1) and extends in the width direction B across a front portion 8a of the crotch region 8 defined between a pair of the leg-openings 13. The lowest elastic 21c is attached to the respective front peripheral edge portion 23a of the respective peripheral portions 23 in the front portion 16 at a relatively high elongation ratio, i.e., under a relatively high tension but attached to the front portion 8a of the crotch region 8 at a relatively low elongation ratio or in a non-stretched state. In consequence, this lowest elastic 21c is in a relaxed state in comparison to the state along the respective front peripheral edge portion 23a.

The rear elastics 22 include a plurality of upper elastics 22a extending in parallel to each other along a peripheral edge portion of the waist-opening 12 and a plurality of lower elastics 22b lying below the upper elastics 22a as viewed in FIG. 1. Of these lower elastics 22b, at least one lowest elastic 22c extends along rear peripheral edge portion 23b of respective peripheral portions 23 of the leg-openings 13 lying in the rear half portion 17 and extends in the width direction B across a rear portion 8b of the crotch region 8 defined between a pair of the leg-openings 13. The lowest elastic 22c is attached to the respective rear peripheral edge portions 23b at a relatively high elongation ratio, i.e., under a relatively high tension, but attached to the rear portion 8b of the crotch region 8 at a relatively low elongation ratio or in a non-stretched state. In consequence, this lowest elastic 22c is in a relaxed state in comparison to the state attached along the respective rear peripheral edge portions 23b.

Referring to FIG. 2, imaginary lines 12b, 12c drawn on the chassis 2 indicate application zones of hot melt adhesive 14 in which the absorbent panel 3 are joined to the topsheet 10a. Referring to FIG. 2, the absorbent panel 3 is joined to the chassis 2 only in these zones indicated by the imaginary lines 12b, 12c and not joined to the chassis 2 in the crotch region 8 and in vicinities thereof.

Figure 3:
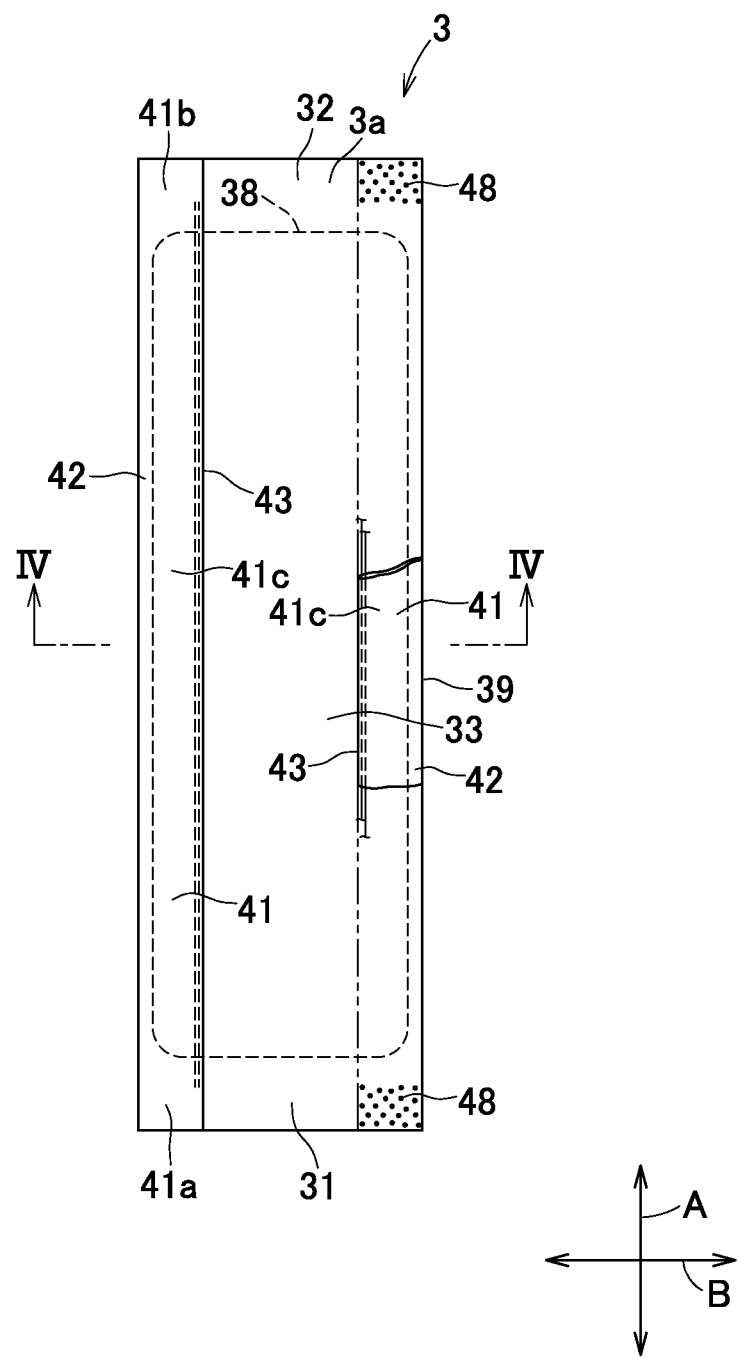
FIG. 3 is a partially cutaway plan view of an absorbent panel.
Figure 4:
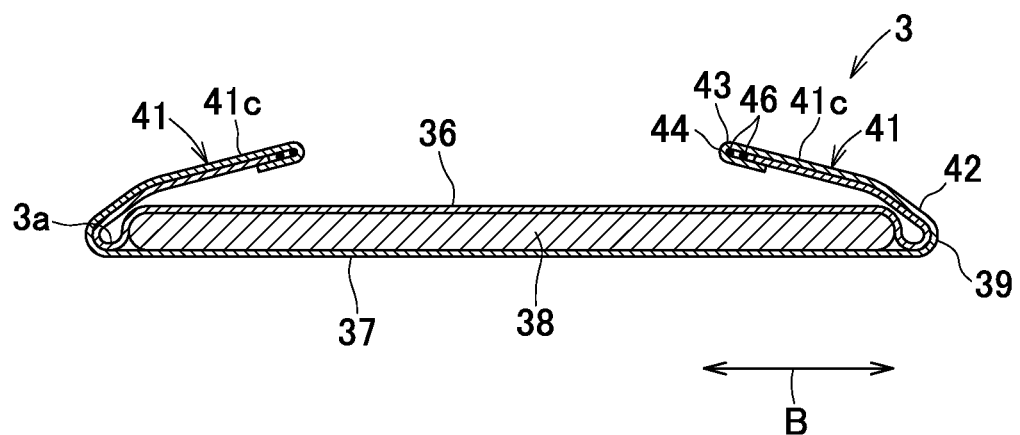
FIG. 4 is a sectional view taken along line IV-IV in FIG. 3.

Of FIGS. 3 and 4, FIG. 3 is the partially cutaway plan view of the absorbent panel 3 and FIG. 4 is the sectional view taken along line IV-IV in FIG. 3. The fluid absorbent panel 3 illustrated in FIG. 3 has the front-back direction A and the width direction B which is the same as those in FIG. 2 and relatively longer in the front-back direction A so as to be defined by a front end portion 31, a rear end portion 32 and the midsection 33 extending between these front and rear end portions 31, 32. Referring to FIG. 4, the absorbent panel 3 includes a liquid-permeable topsheet 36, a liquid-impermeable backsheet 37 and an absorbent core material 38 interposed between these two sheets 36, 37. The topsheet 36 and the backsheet 37 extend outward beyond a periphery of the core material 38 and are put flat together and joined to each other with a hot melt adhesive (not shown) to form a peripheral edge portion 3a of the absorbent panel 3. On the lateral portions in the width direction B of the absorbent panel 3, the topsheet 36 and the backsheet 37 put flat and joined together are folded with the topsheet 36 inside along respective fold edges 39 to form containment flaps 41. Each of the containment flaps 41 has a proximal edge 42 lying in the vicinity of the fold edge 39 and a distal edge 43 extending in parallel to the proximal edge 42. Along the distal edge 43, the backsheet 37 is folded onto itself to form a sleeve 44 within which a single or two or more elastics 46 is or are attached under tension to the sleeve 44. These containment flaps 41 respectively have front end portions 41a and rear end portions 41b joined to the respective inner surface of the front end portions 31 and the rear end portions 32 so that respective midsections 41c of the containment flaps 41 may be spaced upward from the midsection 33 of the absorbent panel 3 under contraction of the elastics 46. The absorbent panel 3 constructed in this manner is placed on the topsheet 10a of the chassis 2 illustrated in FIG. 2 and the front end portion 31 and the rear end portion 32 are joined to the topsheet 10a in the zones indicated by the imaginary lines 12b, 12c with the hot melt adhesive 14.

The chassis 2 of FIG. 2 having the absorbent panel 3 joined thereto may be doubled up along the center line P with the absorbent panel 3 inside and then the lateral edges 6a of the front waist region 6 may be welded to the lateral edges 7a of the rear waist region 7 at the welded seams 11 to obtain the diaper as illustrated in FIG. 1. When the absorbent panel 3 as a component of the diaper 1 formed in this manner is folded along the center line P indicated in FIG. 2 in a U- or V-shape, the midsection 33 placed on the topsheet 10a and folded along the centerline P is moved upward in the crotch region 8 so as to be spaced upward from the topsheet 10a under the contractile effect of the elastics 46 in the respective containment flaps 41 and, as a result, a gap having a dimension D is developed (See FIG. 1). In the diaper 1 illustrated in FIG. 1, the leg-openings 13 in the chassis 2 may be formed to be defined at substantially the same level as the midsection 33 of the absorbent panel 3 located in the crotch region in the height direction C or to be defined at a level lower than the midsection 33.

In such diaper 1 illustrated in FIG. 1, the midsection 33 of the absorbent panel 3 can be freely moved within the chassis 2. In consequence, if the absorbent panel 3 interferes with smooth insertion of the wearer's legs through the leg-openings 13 when the diaper 1 is put on the wearer's body, it is possible for the wearer to move the absorbent panel 3 with the wearer's leg or legs or hand to get out of the way of the wearer's legs. In the diaper 1 having been put on the wearer's body, the bottom elastics 21c and/or 22c of the chassis should not conform to a movement of the absorbent panel 3 so as to move upward or the crotch region 8 of the chassis 2 should not move upward when the absorbent panel 3 is pulled up in order to put the distal edges 43 of the respective containment flaps 41 of the absorbent panel 3 in close contact with the wearer's thighs at a desired fit. Consequently, the bottom elastics 21c and/or 22c and/or the crotch region 8 should not thrust upward the absorbent panel 3 from below the diaper 1 and thereby interfere with spacing away from the topsheet 36 toward the wearer's body of the containment flaps 41.

In this diaper 1, the bottom elastic 21c merely extends in the width direction B in the front section 16 of the diaper 1 without surrounding the leg-openings 13 in an elastically stretched state and this is true also for the bottom elastic 22c. Specifically, an area 51 (See FIG. 2) extending between the front portion 8 and the rear portion 8b of the crotch region 8 corresponding to the area 51 of the chassis 2 facing the wearer's inner thighs and none of elastics extending under tension in the front-back direction of the area 51 facing the wearer's inner thighs in the area 51. As a result, these area 51 should not be elastically put in close contact with the wearer's thighs, more specifically, with the wearer's inner thighs. Such area 51 tend to develop gaps between the area 51 and the wearer's thighs and these gaps can function as breathing regions air-communicating with in- and outsides of the chassis when the diaper 1 illustrated in FIG. 1 is put on the wearer's body. In this way, the area 51 serves to prevent the inside of the chassis 2 from becoming stuffy.

The bottom elastics 21c and 22c are attached at a relatively high elongation ratio along the front and rear peripheral edge portion 23a, 23b of the leg-openings 13 and therefore these portions are under the correspondingly high tension. In contrast, the elastics are attached at relatively low elongation ratio or at no elongation ratio in the front portion 8a and the rear portion 8b of the crotch region 8 and therefore these portions are under the correspondingly low tension or no tension. In the diaper 1 with such arrangement, it is possible to prevent the crotch region 8 from being gathers upon contraction of the elastics having extended under tension in the width direction B, thereby preventing the crotch region 8 from being disfigured. In addition, it is also possible to prevent an apparent dimension in the width direction B of the crotch region from being reduced due to these gathers, thereby preventing the absorbent panel 3 from being visually recognized from the outside of the chassis 2.

In the diaper 1, the front waist region 6 as well as the rear waist region 7 overlaps with the absorbent panel 3 but in zones 6b, 7b (See FIG. 2) in which these waist regions 6, 7 are not joined to the absorbent panel 3, contraction of the front waist elastics 21b and the rear waist elastics 22b are not restrained by the absorbent panel 3 and the front and rear waist regions 6, 7 can be contracted uniformly overall in the width direction B. In such areas 6b, 7b, the gathers 15 are uniformly formed in the width direction B entirely and a dimension in the width direction B, namely, a width dimension also is kept uniform. In consequence, the lateral edge portions 6a, 7a of the chassis 2 rectilinearly extend to ensure the diaper 1 of good appearance.

Figure 5:
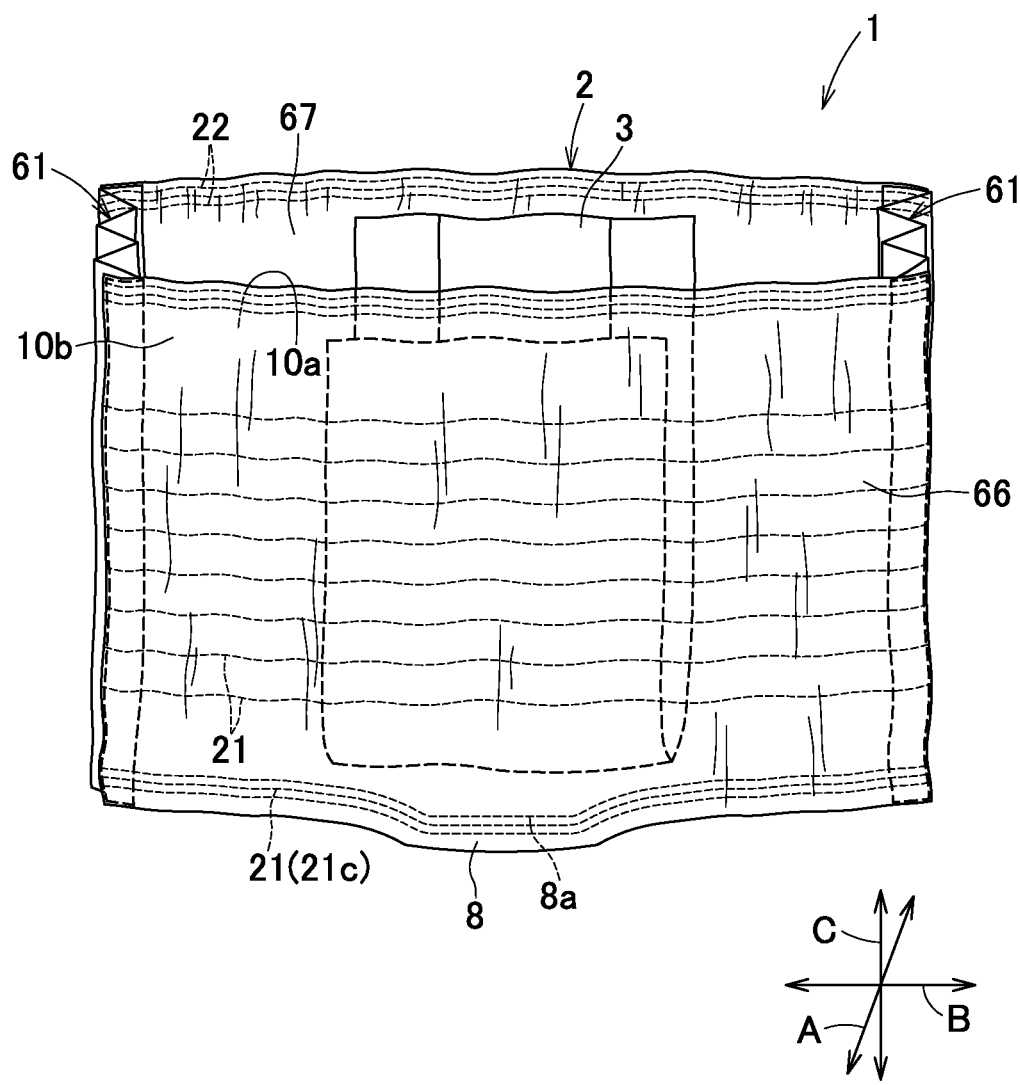
FIG. 5 is a view similar to FIG. 1, exemplifying an embodiment.

FIG. 5 is a view similar to FIG. 1, illustrating another embodiment. The pull-on diaper 1 illustrated in FIG. 5 has the chassis 2 arranged in a manner different from that of the chassis 2 illustrated in FIG. 1. Specifically, in the chassis 2 illustrated in FIG. 5, lateral panels 61 are interposed between a front waist region 66 and a rear waist region 67 and these lateral panels 61 are illustrated to be in folded states, respectively. The front waist region 66 and the rear waist region 67 respectively include the front waist elastics 21 and the rear waist elastics 22 both interposed between the topsheet 10a and the backsheet 10b so that they may be elastically contracted in the width direction B. The lateral panels 61 may be formed of one of an inelastic sheet having no elasticity and an elastic sheet having elasticity.

Figure 6:
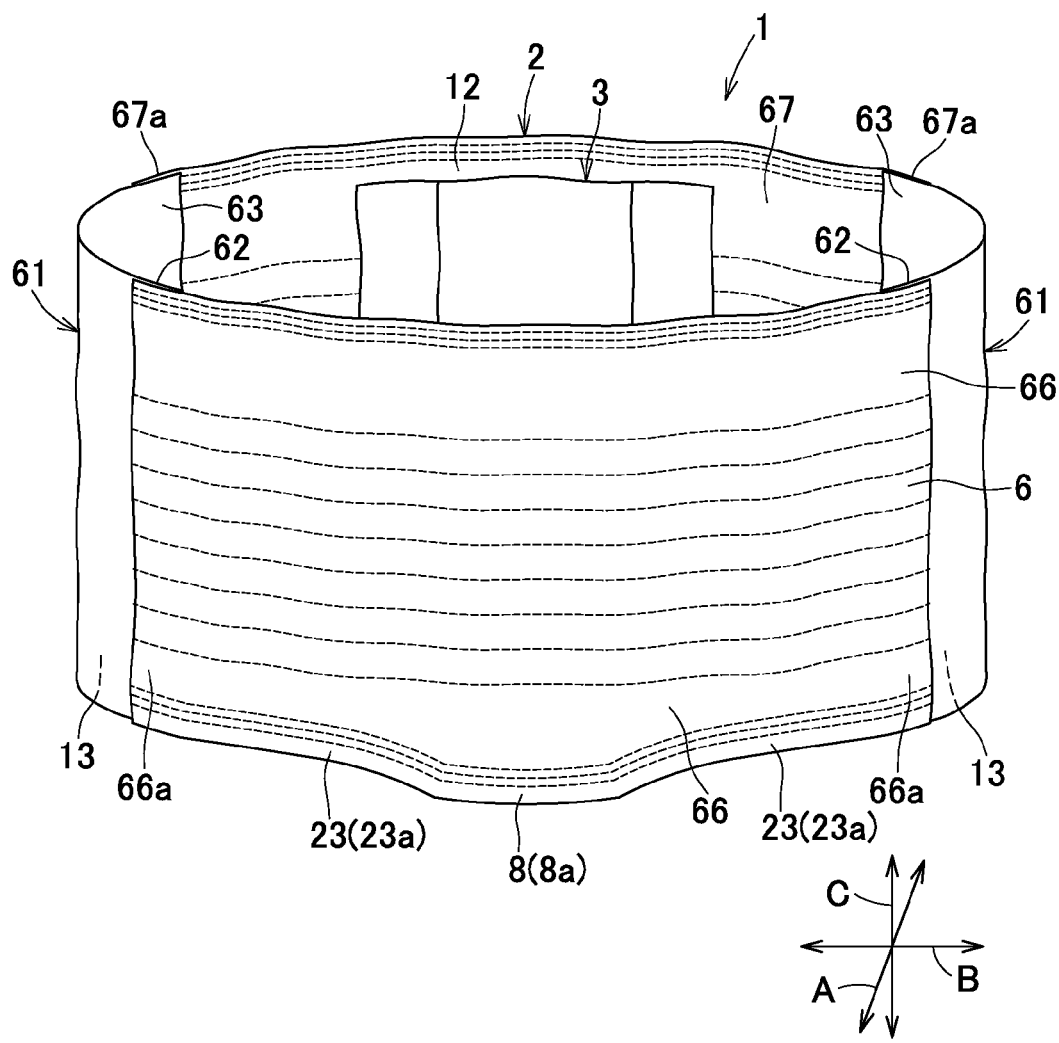
FIG. 6 is a perspective view of the diaper illustrated in FIG. 5, wherein a panel element is in a stretched state.

FIG. 6 is a perspective view of the diaper 1 having the lateral panels 61 circumferentially unfolded from the folded states in FIG. 5 so that the diaper 1 may be put on the wearer's body with the lateral panels 61 unfolded in this manner. In each of the lateral panels 61, lateral edges 62, 63 thereof extending in the vertical direction C are joined to the associated side edge portion 66a of the front waist region 66 and the associated side edge portion 67a of the rear waist region 67. In such diaper 1, the front waist region 6 is defined by the front waist region 66 of the chassis 2 and respective parts of a pair of the lateral panels 61. The waist-opening 12 and the leg-openings 13 are defined by the chassis 2 and a pair of the lateral panels 61.

Figure 7:
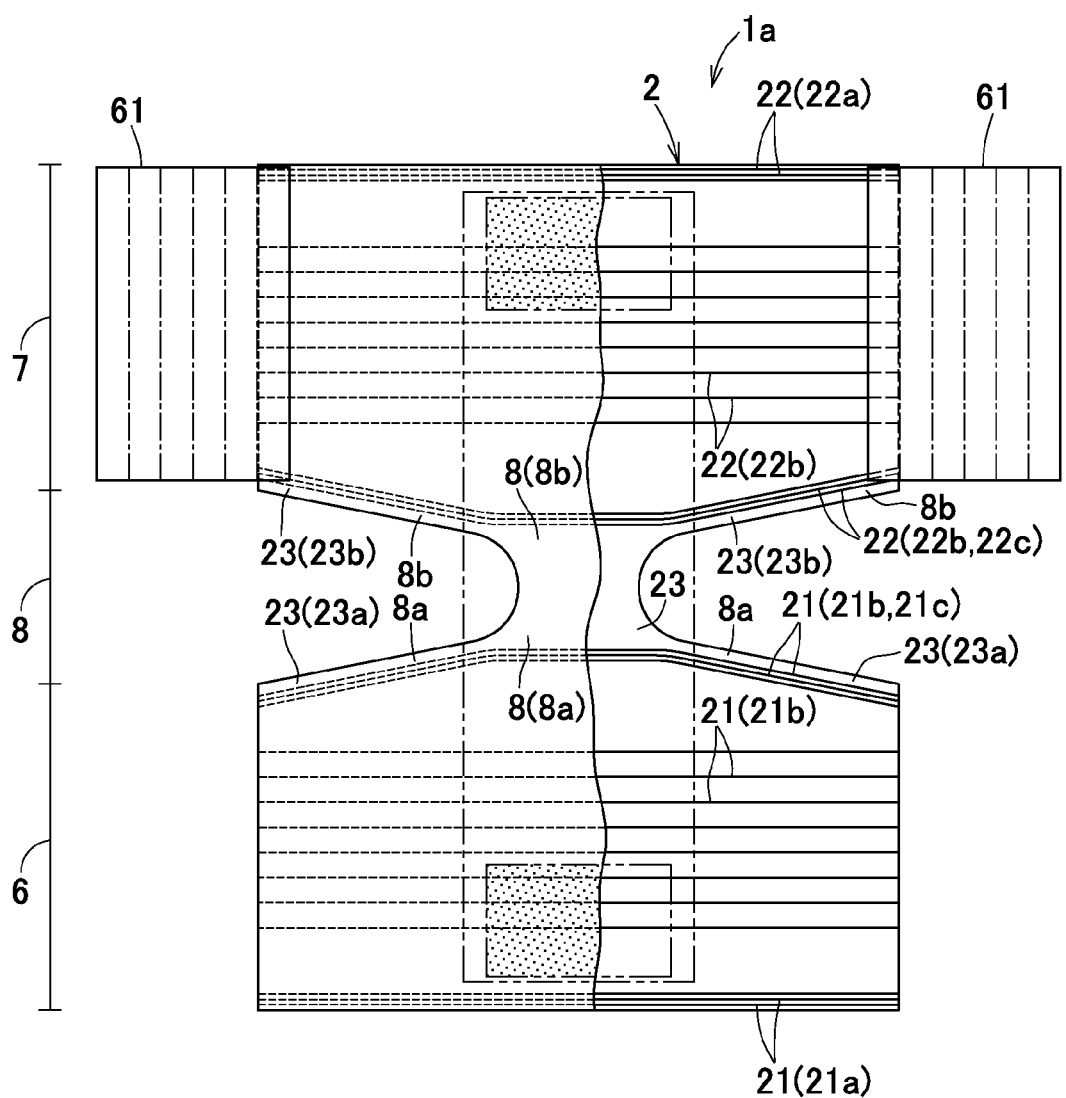
FIG. 7 is a partially cutaway plan view illustrating the diaper of FIG. 6 in its developed state.

FIG. 7 is a partially cutaway plan view illustrating a developed diaper 1a obtained by unsealing the welded seams arranged along the lateral edge portions 66a of the front waist region 66 and the lateral edge portions 62 of the lateral panels 61 in the diaper 1 illustrated in FIG. 6 and developing the diaper 1 in the front-back direction A and the width direction B. The chassis 2 in the developed diaper 1a is similar to the developed diaper 1a illustrated in FIG. 2 so long as the chassis 2 includes the topsheet 10a, the backsheet 10b, the front waist elastics 21 and the rear waist elastics 22. In this regard, in the developed diaper 1a illustrated in FIG. 7, the bottom elastics 21c, 22c are present only in the front peripheral edge portion 23a and the rear peripheral edge portion 23b of the leg-openings defined by the chassis 2. The bottom elastics 21c, 22c arranged in the manner as illustrated in FIG. 6 also can function in the same manner as the bottom elastics 21c, 22c illustrated in FIG. 1.

In the exemplified pull-on diaper 1, as material of the topsheet 10a and the backsheet 10b of the chassis 2, for example, a nonwoven fabric or a woven fabric formed of thermoplastic synthetic fibers, a film formed of a thermoplastic synthetic resin, a laminate of two or more nonwoven fabric sheets or a laminate of a nonwoven fabric and a film may be used. The topsheet 10a and the backsheet 10b are preferably breathable and more preferably breathable but liquid-impermeable. As material of the liquid-permeable topsheet 36 in the absorbent panel 3, a nonwoven fabric formed of thermoplastic synthetic fibers or perforated film formed of thermoplastic synthetic resin may be used. As material of the liquid-impermeable backsheet 37, a film formed of thermoplastic synthetic resin may be used. As the core material 38 in the absorbent panel 3, water absorbent material such as fluff wood pulp or a mixture of fluff wood pulp and superabsorbent polymer particles wrapped with a wrapping sheet formed of tissue paper or a liquid-permeable nonwoven fabric.

The pull-on wearing article exemplified hereinbefore on the basis of the disposable pull-on diaper 1 can be implemented also, for example, in the form of incontinent patient pant or toilet-training pant.

REFERENCE SIGNS LIST 1 disposable pull-on wearing article (diaper)
2 chassis
3 absorbent panel
6 front waist region
7 rear waist region
8 crotch region

The invention claimed is:

1. A disposable pull-on wearing article comprising:
    a pant-shaped chassis including a front waist region, a rear waist region and a crotch region each having an inner side facing a wearer's skin; and
    an absorbent panel extending across the crotch region into the front waist region and the rear waist region and joined to the inner side of the chassis, wherein the chassis is formed with a waist-opening and a pair of leg-openings, wherein:
    the chassis includes a front portion including the front waist region and a part of the crotch region and a rear portion including the rear waist region and a part of the crotch region;
    the front portion is provided with a plurality of front waist elastics extending in a width direction of the front waist region and spaced apart from each other in a vertical direction of the front waist region;
    at least one front lowest elastic lying at a bottom of the front waist elastics is disposed in a stretched state along front peripheral edge portion of the pair of leg-openings and, in a front portion of the crotch region defined between the pair of leg-openings, the at least one front lowest elastic is disposed in a more relaxed state than along the front peripheral edge portions;
    the rear portion is provided with a plurality of rear waist elastics extending in a width direction of the rear waist region and spaced apart from each other in a vertical direction of the rear waist region;
    at least one rear lowest elastic lying at a bottom of the rear waist elastics is disposed in a stretched state along rear peripheral edge portions of the pair of leg-openings and, in a rear portion of the crotch region defined between the pair of leg-openings, the at least one rear lowest elastic is disposed in a more relaxed state than along the rear peripheral edge portions;
    the absorbent panel includes a front end portion joined to an inner surface of the front waist region, rear end portion joined to an inner surface of the rear waist region and a midsection extending between the front end portion and the rear end portion and not joined to an inner surface of the crotch region, said midsection being freely movable within said chassis; and
    the absorbent panel is formed on lateral portions in the width direction thereof with containment flaps adapted to be spaced away from the inner surface of the absorbent panel toward a wearer under contraction of elastics extending between the front end portion and the rear end portion.

2. The wearing article according to claim 1, wherein opposite lateral portions in the width direction of the chassis extend in the vertical direction to a lower end portion of the absorbent panel located in the crotch region.

3. The wearing article according to claim 2, wherein the opposite lateral portions in the width direction of the chassis are prepared separately of the elements forming the front and rear waist regions and panel elements including neither the front waist elastics nor the rear waist elastics are interposed between the front waist region and the rear waist region.

4. The wearing article according to claim 3, wherein the bottom elastic in the front waist elastics and the bottom elastic in the rear waist elastics extend across the crotch region but not to inner thigh areas of the crotch region.

5. The wearing article according to claim 4, wherein the inner thigh areas of the crotch region include none of elastics extending in front-back direction in a stretched state.

6. The wearing article according to claim 3, wherein a portion of the front waist region defined below the front end portion of the absorbent panel is uniformly formed with gathers in the entire width direction and a width of this portion of the front waist region is uniform.

7. The wearing article according to claim 2, wherein the bottom elastic in the front waist elastics and the bottom elastic in the rear waist elastics extend across the crotch region but not to inner thigh areas of the crotch region.

8. The wearing article according to claim 7, wherein the inner thigh areas of the crotch region include none of elastics extending in front-back direction in a stretched state.

9. The wearing article according to claim 7, wherein a portion of the front waist region defined below the front end portion of the absorbent panel is uniformly formed with gathers in the entire width direction and a width of this portion of the front waist region is uniform.

10. The wearing article according to claim 2, wherein a portion of the front waist region defined below the front end portion of the absorbent panel is uniformly formed with gathers in the entire width direction and a width of this portion of the front waist region is uniform.

11. The wearing article according to claim 1, wherein the opposite lateral portions in the width direction of the chassis are prepared separately of the elements forming the front and rear waist regions and panel elements including neither the front waist elastics nor the rear waist elastics are interposed between the front waist region and the rear waist region.

12. The wearing article according to claim 11, wherein the bottom elastic in the front waist elastics and the bottom elastic in the rear waist elastics extend across the crotch region but not to inner thigh areas of the crotch region.

13. The wearing article according to claim 12, wherein the inner thigh areas of the crotch region include none of elastics extending in front-back direction in a stretched state.

14. The wearing article according to claim 12, wherein a portion of the front waist region defined below the front end portion of the absorbent panel is uniformly formed with gathers in the entire width direction and a width of this portion of the front waist region is uniform.

15. The wearing article according to claim 11, wherein a portion of the front waist region defined below the front end portion of the absorbent panel is uniformly formed with gathers in the entire width direction and a width of this portion of the front waist region is uniform.

16. The wearing article according to claim 1, wherein the bottom elastic in the front waist elastics and the bottom elastic in the rear waist elastics extend across the crotch region but not to inner thigh areas of the crotch region.

17. The wearing article according to claim 16, wherein the inner thigh areas of the crotch region include none of elastics extending in front-back direction in a stretched state.

18. The wearing article according to claim 16, wherein a portion of the front waist region defined below the front end portion of the absorbent panel is uniformly formed with gathers in the entire width direction and a width of this portion of the front waist region is uniform.

19. The wearing article according to claim 1, wherein a portion of the front waist region defined below the front end portion of the absorbent panel is uniformly formed with gathers in the entire width direction and a width of this portion of the front waist region is uniform.

20. The wearing article according to claim 1, wherein a portion of the rear waist region defined below the rear end portion of the absorbent panel is uniformly formed with gathers in the entire width direction and a width of this portion of the rear waist region is uniform.

* * * * *